United States Patent
Hoshino et al.

(10) Patent No.: US 8,091,425 B2
(45) Date of Patent: Jan. 10, 2012

(54) ULTRASONIC TESTING METHOD OF THREADED JOINT OF PIPES OR TUBES

(75) Inventors: Ikuji Hoshino, Osaka (JP); Masaki Yamano, Osaka (JP); Shigeo Nagasaku, Osaka (JP)

(73) Assignees: Sumitomo Metal Industries, Ltd., Osaka (JP); Vallourec Mannesmann Oil & Gas France, Aulnoye-Aymeries (FR)

( * ) Notice: Subject to any disclaimer, the term of this patent is extended or adjusted under 35 U.S.C. 154(b) by 84 days.

(21) Appl. No.: 12/311,162

(22) PCT Filed: Sep. 14, 2007

(86) PCT No.: PCT/JP2007/068592
§ 371 (c)(1),
(2), (4) Date: Nov. 3, 2009

(87) PCT Pub. No.: WO2008/035794
PCT Pub. Date: Mar. 27, 2008

(65) Prior Publication Data
US 2010/0107766 A1  May 6, 2010

(30) Foreign Application Priority Data

Sep. 21, 2006 (JP) ................... 2006-255975

(51) Int. Cl.
G01N 29/07 (2006.01)
G01N 29/11 (2006.01)
G01N 29/40 (2006.01)
G01N 29/48 (2006.01)

(52) U.S. Cl. .............. 73/598; 73/622; 73/625; 73/626; 73/628; 73/600

(58) Field of Classification Search .............. 73/599, 73/600, 622, 625, 626, 628, 597, 598
See application file for complete search history.

(56) References Cited

U.S. PATENT DOCUMENTS

| 4,870,866 A | 10/1989 | Slack |
| 6,438,814 B1 * | 8/2002 | Seymour et al. ........... 29/407.02 |
| 2005/0256676 A1 * | 11/2005 | Ales et al. ................... 702/159 |

FOREIGN PATENT DOCUMENTS

| JP | 61-187648 | | 8/1986 |
| JP | 63298054 A | * | 12/1988 |
| JP | 1-235848 | | 9/1989 |
| JP | 9-152425 | | 6/1997 |
| JP | 10-267175 | | 10/1998 |
| JP | 2001-108662 | | 4/2001 |
| JP | 3605253 | | 10/2004 |
| SU | 905778 B | * | 2/1982 |

* cited by examiner

OTHER PUBLICATIONS

A. Narita et al., "Sumitomo's Premium Connection "VAM ACE" for OCTG", Sumitomo Metals, Jan. 1994, vol. 46, No. 1, pp. 65-73.

Primary Examiner — Hezron E Williams
Assistant Examiner — Rose M Miller
(74) Attorney, Agent, or Firm — Clark & Brody

(57) ABSTRACT

An ultrasonic testing method relates to a threaded joint of pipes including a pin having an external thread part, a metal seal part, and a shoulder part on an outer peripheral surface, and a box having an internal thread part, a metal seal part, and a shoulder part with the box and pin being fastened together using a lubricant. The method includes transmitting and receiving ultrasonic waves to and from a plurality of locations along an axial direction of the threaded joint in at least one of the internal thread part, the metal seal part, and the shoulder part of the box; detecting echo intensities and reception times of echoes for the plurality of locations; and detecting an abnormal portion in the threaded joint based on a longitudinal axial directional distribution of the echo intensities and longitudinal axial directional distribution of reception times of the echoes.

3 Claims, 9 Drawing Sheets

Fig. 4A
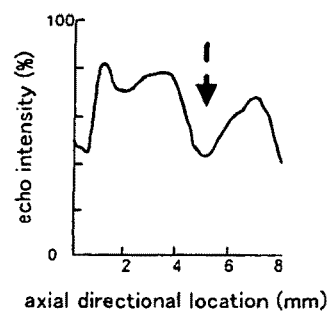
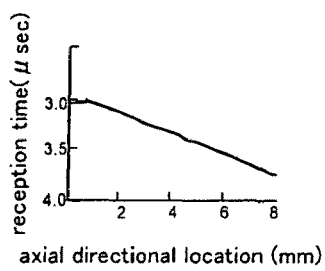
Fig. 4B
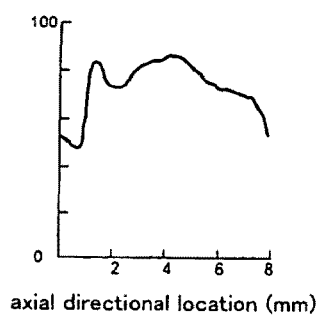
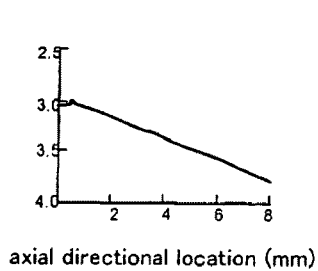
Fig. 4C
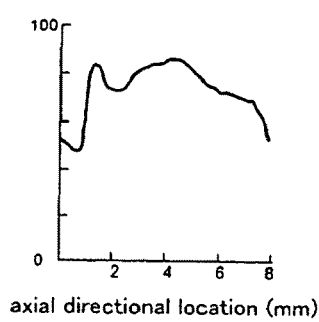
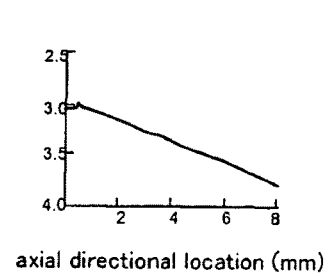
Fig. 4D
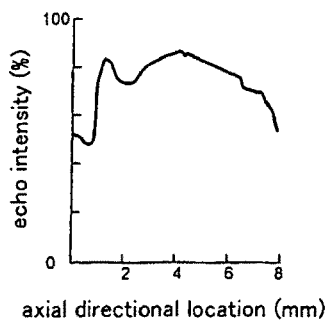
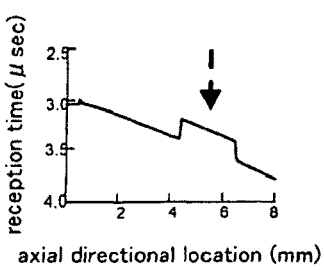
Fig. 4E
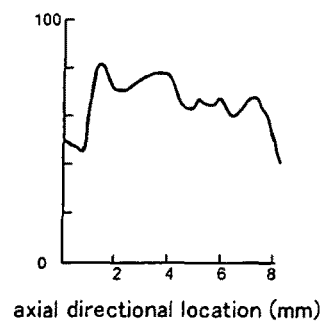
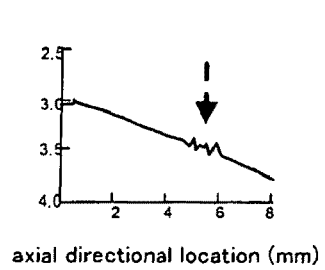

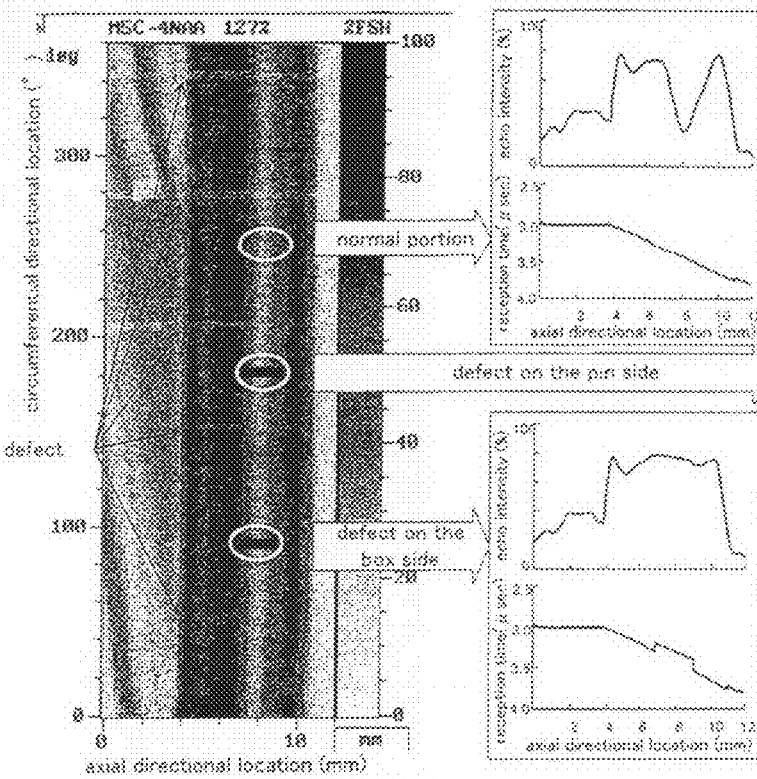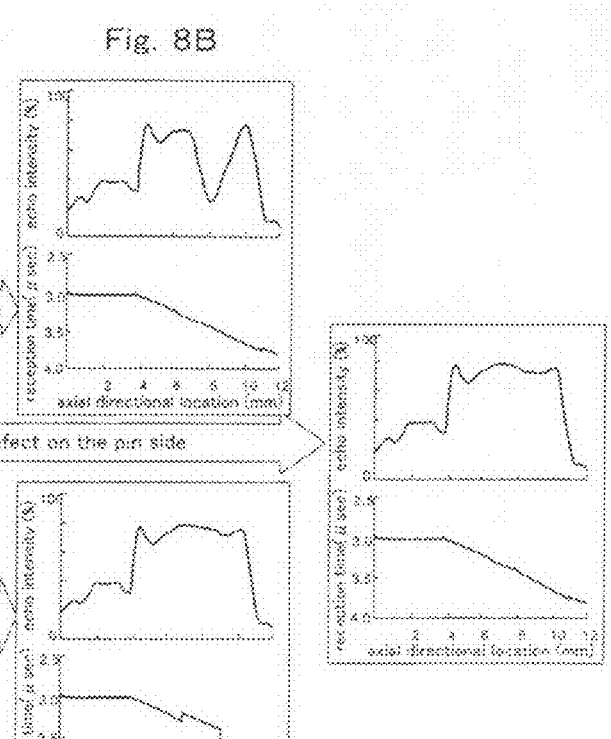

ULTRASONIC TESTING METHOD OF THREADED JOINT OF PIPES OR TUBES

BACKGROUND OF THE INVENTION

1. Field of the Invention

The present invention relates to a method for detecting an abnormal portion (defect, non-adhering portion, and seized portion) located at a contact region between each part of a pin and each part of a box forming a threaded joint to be used as a joint of pipes or tubes such as Oil Country Tubular Goods (OCTG). Hereinafter, "pipes or tubes" are referred to as "pipes" when deemed appropriate.

2. Description of the Related Art

Conventionally, as a joint for OCTG, a threaded joint has been widely used. FIG. 1 is an axial directional cross sectional view that schematically illustrates a general structure of a threaded joint. As shown in FIG. 1, a threaded joint 100 is provided with a pin 1 having an external thread part 11, a metal seal part 12, a shoulder part 13 on an outer peripheral surface, and a box 2 having an internal thread part 21, a metal seal part 22, and a shoulder part 23 corresponding to each part of the pin 1 on an inner peripheral surface and being fastened with the pin 1.

The external thread part 11 and the internal thread part 21 (hereinafter, these parts are generally named as "thread parts 11, 21") are screwed with each other so as to effect a function for fastening the pin 1 and the box 2. The external diameter of the metal seal part 12 is slightly larger than the internal diameter of the metal seal part 22 (this difference is referred to as "an interference margin"), and when the pin 1 is fastened with the box 2, due to the interference margin, a surface pressure is generated on a contact region between the both metal seal parts 12, 22 and due to this contact surface pressure, a function to sufficiently hold an air leakage efficiency of the threaded joint 100 is effected. The shoulder parts 13, 23 effect a function to prevent a high contact surface pressure such that an excess plastic transformation is generated from being generated on the metal seal parts 12, 22 and secure sufficient screwing amount so as to ascertain fastening of the threaded joint 100. Further, not only on the metal seal parts 12, 22 but also on the thread parts 11, 21, the threaded joint 100 may have the same interference margin as the metal seal parts 12, 22 in order to secure screwing of the thread parts 11, 21 so that they are not easily loosened. In this case, the shoulder parts 13, 23 also effect a function to limit the interference margins of the thread parts 11, 21 into a safe area so as to prevent an excess stress on the box 2.

As a method for evaluating a fastening state of a threaded joint having the above-described structure, conventionally, a method for monitoring change of a torque to be generated when fastening a threaded joint has been widely used (for example, refer to Japanese Patent Application Laid-Open No. 10-267175). FIG. 2 is an explanatory view for explaining a conventional method for evaluating a fastening state of a threaded joint. As shown in FIG. 2, as fastening of the threaded joint has been progressed in series, due to a frictional resistance due to interference of the thread parts 11, 21 and interference of the metal seal parts 12, 22, a torque is generated. Then, due to abutting of the shoulder parts 13, 23, the torque rapidly rises. Conventionally, good and bad of the fastening state of the threaded joint is determined by monitoring this change of the torque by an operator. In other words, in the case that the torque rises more than a predetermined threshold value, judging that the shoulder parts 13, 23 abut against with each other, it is determined that the fastening of the threaded joint 100 has been sufficiently completed.

However, according to the conventional evaluating method shown in FIG. 2, the fact that the thread parts 11, 21 interfere with each other, the metal seal parts 12, 22 interfere with each other, and the shoulder parts 13, 23 abut against with each other in face is not evaluated by measuring any physical amount independently and respectively. This is absolutely a method based on a past empirical rule such that a torque is generated because respective parts adhere tightly (interfere or abut) with each other. It is true that a torque is generated when the respective parts adhere tightly (interfere or abut) with each other. However, a large torque may be generated also due to another cause such as seizing of the thread parts 11, 12. Therefore, only by monitoring change of a torque, it is difficult to evaluate the fastening state with a high degree of accuracy (evaluate whether the respective parts 11, 12, and 13 of the pin 1 and the respective parts 21, 22, and 23 of the box 2 are in adhering states or non-adhering states).

Further, even when there is a defect (flaw) that may damage an air leakage efficiency of the threaded joint 100 at the contact region between the respective parts 11, 12, and 13 of the pin 1 and the respective parts 21, 22, and 23 of the box 2 forming the threaded joint 100, it is difficult for change of a torque caused by this defect (flaw) to be generated. Therefore, according to a conventional evaluating method shown in FIG. 2, the defect cannot be detected.

As a method for detecting a defect or an non-adhering portion of a plurality of members, there is publicly known an ultrasonic testing method using reflection of an ultrasonic wave from the defect or the non-adhering portion. Also upon detection of the defect or the non-adhering portion located at a contact region between the pin 1 and the box 2, it may be considered to use this ultrasonic testing method.

Conventionally, for example, as a measurement method using reflection of a ultrasonic wave with respective to a threaded joint of pipes, a method for measuring a contact surface pressure at a contact region between the pin and the box by measuring a reflectance of the ultrasonic wave at the contact region is disclosed in the specification of U.S. Pat. No. 4,870,866.

However, the art described in the specification of U.S. Pat. No. 4,870,866 merely discloses a method for measuring a contact surface pressure at a contact region between a pin and a box, and neither disclosure nor suggestion is made with respect to a method for detecting the defect or the non-adhering portion located at the contact region.

In addition, as an inspection method of a bonded surface of clad steel, JIS G 0601-1989, "testing method of clad steel" using the principle of reflection and passage of an ultrasonic wave on the bonded surface has been put into practical use. More practically, in the above-mentioned JIS standard, an intensity of the first; bottom echo is adjusted to 80%. The first bottom echo is obtained by the first time reflection of the ultrasonic wave passing through a normal portion (namely, bonded portion) in a bonded surface of a plate material from a bottom surface of the plate material. When a portion has the intensity of the first bottom echo not more than 5% and an echo from this portion is mainly received, such a portion is defined as a non-bonded portion.

However, since the above-mentioned JIS standard is a method for inspecting a bonded surface based on change in intensity of the bottom echo of the plate material as described above, this method is difficult to be applied for a threaded joint that cannot obtain the bottom echo. The reason that a threaded joint cannot obtain the bottom echo is because the contact region between the pin and the box is not parallel to the inner peripheral surface of the pin. In addition, since the above-mentioned JIS standard is just a method for detecting a non-bonded portion without assumption that there is a defect (flaw) on the bonded surface, it is difficult to identify whether a reflectance or the like is changed due to existence of a defect on the bonded surface or due to existence of a non-bonded portion (namely, non-adhering portion) on the bonded surface.

It is important for quality control of the threaded joint to identify whether the abnormal portion located on the contact region between each part of the pin and each part of the box forming the threaded joint is a non-adhering portion or a defect. A non-adhering portion may be generated due to shortage of fastening or a dimension error of the box and the pin, or the like. On the other hand, a defect may be generated due to a flaw found on the box or the pin before contact, biting of an impure substance into the contact region, progress of seizing with shortage of a lubricant lying between the box and the pin, or the like. By identifying a non-adhering portion and a defect, it is possible to carry out appropriate quality control in accordance with a kind of the abnormal portion. When the abnormal portion is identified as being a non-adhering portion, it is possible to reconsider a fastening condition or a dimension tolerance of the threaded joint, while, when the abnormal portion is identified as being a defect, it is possible to discard and exchange the defected threaded joint.

SUMMARY OF THE INVENTION

The present invention has been made for solving the foregoing problems in the conventional art, and an object of the present invention is to provide a method for detecting an abnormal portion (defect, non-adhering portion, and seized portion) located at a contact region between each part of a pin and each part of a box forming a threaded joint to be used as a joint of pipes or tubes such as OCTG.

As a result of concentrated consideration by the inventors of the present invention in order to solve the above-described problems, the inventors have reached the following knowledge.

(1) The thickness of the lubricant lying at the contact region between each part (an external thread part, a metal seal part, and a shoulder part) of the pin and each part (an internal thread part, a metal seal part, and a shoulder part) of the box is locally changed in accordance with a fastening state of these respective parts. Specifically, in a state where the threaded joint is normal (namely, there are no defect and seized portion at the contact region of the threaded joint) and each part of the pin and each part of the box adhere tightly with each other (for example, an outer diameter of the metal seal part 12 is slightly larger than an inner diameter of the metal seal part 22), unlike the non-adhering state (for example, the outer diameter of the metal seal part 12 is smaller than the inner diameter of the metal seal part 22), no lubricant locally lies.

(2) In accordance with existence or nonexistence of the lying lubricant, the echo intensity of the ultrasonic wave is changed. Specifically, the echo intensity of the ultrasonic wave received from a location where the lubricant does not substantially lie is lower than the echo intensity of the ultrasonic wave received from a location where the lubricant lies.

(3) In a state where a defect or a seized portion lies in the location where the lubricant would not substantially lie (namely, the location where the echo intensity of the ultrasonic wave would be lower) if the threaded joint were normal and each part of the pin and each part of the box adhered tightly with each other, the echo intensity of the ultrasonic wave becomes higher than a state where a defect and a seized portion do not lie.

(4) Reception time of the echo from a defect lying in the box or the echo from a seized portion between the box and the pin (namely, time from transmission of the ultrasonic wave to reception thereof) is shorter than the reception time of the echo from a normal threaded joint in an adhering state, the echo from a threaded joint in a non-adhering state, or the echo from a defect lying in the pin.

The present invention has been completed based on the above-described knowledge of the inventors. The present invention provides an ultrasonic testing method of a threaded joint of pipes or tubes including a pin having an external thread part, a metal seal part, and a shoulder part on an outer peripheral surface, and a box having an internal thread part, a metal seal part, and a shoulder part corresponding to each part of the pin on an inner peripheral surface and being fastened with the pin by way of a lubricant, the method comprising the steps of: transmitting and receiving ultrasonic waves to and from a plurality of locations along an axial direction of the threaded joint in at least one of the internal thread part, the metal seal part, and the shoulder part of the box; detecting echo intensities and reception times of echoes for the plurality of locations; and detecting an abnormal portion in the threaded joint based on axial directional distribution of the echo intensities and axial directional distribution of reception times of the echoes.

According to the present invention, ultrasonic waves are transmitted and received to and from a plurality of locations along an axial direction of a threaded joint in at least one part among an external thread part, a metal seal part, and a shoulder part of a box included in the threaded joint (hereinafter, appropriately referred to as "a part to be evaluated"). As described above, the thickness of the lubricant lying at the contact region between each part of the pin and each part of the box is locally thin along the axial direction of the threaded joint in a state where the respective parts adhere tightly with each other, and the echo intensity of the ultrasonic wave received from the location where the lubricant does not substantially lie is lower than the echo intensity of the ultrasonic wave received from the location where the lubricant lies. As a result, when the ultrasonic waves are transmitted and received to and from the plurality of locations along the axial direction of the threaded joint in the respective parts of the box, in a state where each part of the box and each part of the pin adhere tightly with each other, the echo intensity of the ultrasonic wave is distributed in the axial direction in such a manner that the echo intensity of the ultrasonic wave from the location where the lubricant at the contact region does not substantially lie is locally lower while the echo intensity of the ultrasonic wave from the remaining locations is higher. On the other hand, in a state where each part of the box and each part of the pin do not adhere tightly with each other, since the lubricant lie at the entire contact region of the respective parts, the echo intensity of the ultrasonic wave is distributed in the axial direction in such a manner of being higher across the entire areas of the respective parts.

In addition, even in a state where the defect or the seized portion lies in the location where the lubricant would not substantially lie (namely, the location where the echo intensity of the ultrasonic wave would be lower) if each part of the pin and each part of the box adhered tightly with each other as described above, the echo is reflected from the defect or the seized portion, so that the echo intensity of the ultrasonic wave is distributed in the axial direction in such a manner of being higher across the all areas of the respective parts.

Therefore, based on the axial directional distribution of the echo intensities detected for the plurality of locations, it is possible to detect an abnormal portion (defect, non-adhering portion, and seized portion) lying in the part to be evaluated of the threaded joint. Specifically, for example, when a ratio (minimum value/standard value) between the minimum value of the echo intensity and the standard value of the echo intensity exceeds a predetermined threshold value with respect to the axial directional distribution of the echo intensities from the part to be evaluated, it is possible to determine that the abnormal portion lies. As the standard value, the echo intensity that is hardly changed even when the fastening state (adhering state or non-adhering state) is changed may be used. Alternatively, it is also possible to determine that the abnormal portion lies in a case where the axial directional length in the area of the echo intensity being not more than a predetermined threshold value becomes not more than a predetermined length.

In addition, as described above, the reception time of the echo from the defect lying in the box or the echo from the seized portion between the box and the pin (namely, time from transmission of the ultrasonic wave to reception thereof) is shorter than the reception time of the echo from the normal threaded joint in the adhering state, the echo from the threaded joint in the non-adhering state, or the echo from the defect lying in the pin. Accordingly, based on the axial directional distribution of the reception times of the echo detected for the plurality of locations, it is possible to identify the abnormal portion lying in the part to be evaluated of the threaded joint (defect lying in the box and seized portion between the box and the pin can be identified from other abnormal portions). Specifically, for example, by obtaining a difference between the axial directional distribution of the reception times of the echoes from the part to be evaluated and the axial directional distribution of the reception times of the echoes that has been obtained in advance for the normal threaded joint in the adhering state, it is possible to determine that there is a defect lying in the box or a seized portion particularly among the abnormal portions when the axial directional length of an area where the difference exceeds a predetermined threshold value exceeds a predetermined length.

Further, as a method for transmitting and receiving the ultrasonic waves to and from a plurality of locations along the axial direction of the threaded joint in at least one part of the box, for example, there is considered a method for relatively moving an ultrasonic probe in the axial direction of the threaded joint.

Alternatively, it is also possible to employ a method for electrically controlling the transmission and reception of the ultrasonic wave by each transducer of an ultrasonic phased array probe in which a plurality of transducers are arrayed.

According to the ultrasonic testing method of the threaded joint of pipes or tubes of the present invention, it is possible to detect with a high degree of accuracy the abnormal portion (defect, non-adhering portion, and seized portion) lying at the contact region between each part of the pin and each part of the box forming the threaded joint to be used as the joint of pipes or tubes such as OCTG.

BRIEF DESCRIPTION OF THE DRAWINGS

FIG. 4 (FIG. 4A, FIG. 4B, FIG. 4C, FIG. 4D and FIG. 4E) is a graph showing an example of the axial directional distribution of echo intensities and the axial directional distribution of reception times of an echoes that are obtained with respect to the metal seal part of the box;

FIG. 8 illustrates an example of a result of the ultrasonic testing of the metal seal part in an adhering state by using the ultrasonic testing apparatus.

DETAILED DESCRIPTION OF THE PREFERRED EMBODIMENT

Hereinafter, with reference to the attached drawings, an embodiment of an ultrasonic testing method of a threaded joint of pipes or tubes according to the present invention will be described.

First, knowledge obtained by the inventors of the present invention in a process of reaching the present invention will be described in detail.

Figure 1:
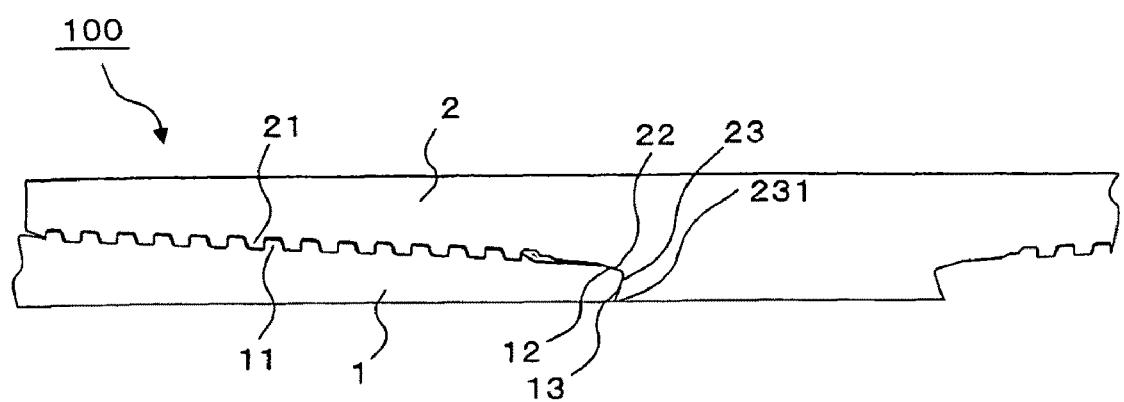
FIG. 1 is a cross sectional view in an axial direction that schematically illustrates a general constitution of a threaded joint.
Figure 2:
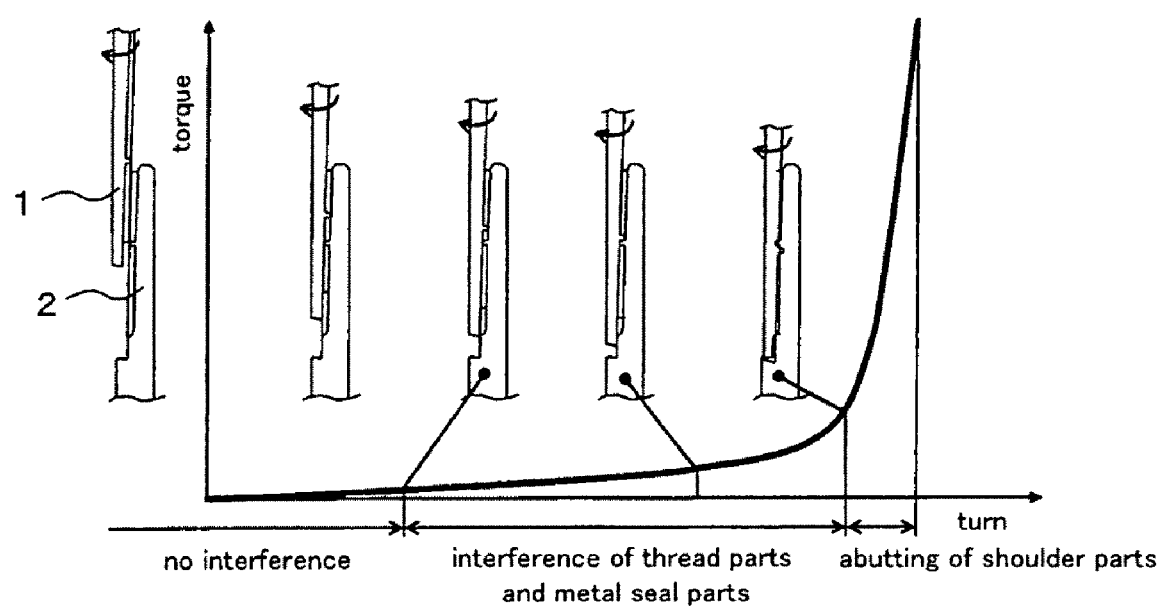
FIG. 2 is an explanatory view for describing a conventional method for evaluating a fastening state of a threaded joint.

The inventors of the present invention conducted a test for evaluating an axial directional distribution of echo intensities and an axial directional distribution of reception times of echoes obtained by transmitting and receiving an ultrasonic wave from and to each part of a box 2 and scanning transmission and reception positions of the ultrasonic wave in an axial direction of a threaded joint 100. The test was conducted with respect to each of a case where each part of a pin 1 (an external thread part 11, a metal seal part 12, and a shoulder part 13) and each part of a box 2 (an internal thread part 21, a metal seal part 22, and a shoulder part 23) forming the threaded joint 100 shown in FIG. 1 are fastened in an adhering state, a case where they are fastened in a non-adhering state, a case where a defect is formed in the pin 1, a case where a defect is formed in the box 2, and a case where seized portion is generated between the pin 1 and the box 2.

FIG. 3 is an explanatory view for illustrating a brief summary of a test for evaluating an axial directional distribution of echo intensities and an axial directional distribution of reception times of echoes, the test being conducted for the metal seal part 22 of the box 2. FIG. 3A illustrates a brief summary of an evaluation test in a case where the metal seal part 22 of the box 2 and the metal seal part 12 of the box 1 are fastened in an adhering state (namely, a state where an outer diameter of the metal seal part 12 is slightly larger than an inner diameter of the metal seal part 22). FIG. 3B illustrates a brief summary of the evaluation test in a case where the metal seal parts 12 and 22 are fastened in a non-adhering state (namely, a state where the outer diameter of the metal seal part 12 is smaller than the inner diameter of the metal seal part 22). FIG. 3C illustrates a brief summary of the evaluation test in a case where an artificial defect (slit) F1 having an axial length of 2 mm, a circumferential directional length of 1 mm, and a depth of 0.5 mm is provided on a seal face of the metal seal part 12 and the metal seal parts 12 and 22 would be fastened in an adhering state if the artificial defect F1 were not provided. FIG. 3D illustrates a brief summary of the evaluation test in a case where an artificial defect (slit) F2 having an axial length of 2 mm, a circumferential directional length of 1 mm, and a depth of 0.5 mm is provided on the seal face of the metal seal part 22 and the metal seal parts 12 and 22 would be fastened in an adhering state if the artificial defect F2 were not provided. FIG. 3E illustrates a brief summary of the evaluation test in a case where seized portion F3 is generated between the metal seal parts 12 and 22 and the metal seal parts 12 and 22 would be fastened in an adhering state if the seized portion F3 were not generated.

Specifically, in each of the cases of FIGS. 3A to 3E, evaluation is made to an axial directional distribution of the echo intensities and an axial directional distribution of the reception times of the echoes obtained by scanning the transmission and reception positions of the ultrasonic wave in the axial direction of the threaded joint 100 through transmitting and receiving the ultrasonic wave so as to be focused on a center portion of the seal face of the metal seal part 22 in the box (outer diameter: about 150 mm, inner diameter: about 125 mm) and moving an ultrasonic probe in the axial direction of the threaded joint 100. As the ultrasonic probe, an immersion probe (frequency: 5 MHz, transducer diameter: about 19 mm, focal distance: about 64 mm, point focus probe) is used. An angle of the ultrasonic probe is adjusted so that the transmitted ultrasonic wave propagates normal to the seal face of the metal seal part 22. In addition, a lubricant is laid between the pin 1 and the box 2.

FIG. 4 is a graph showing an example of the axial directional distribution of the echo intensities and the axial directional distribution of the reception times of the echoes that are obtained from the evaluation test with respect to the metal seal part 22 of the box 2.

Figure 3A:
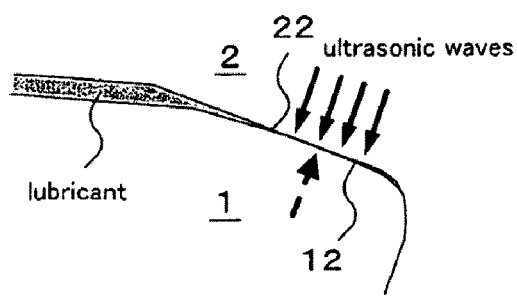
FIG. 3 (FIG. 3A, FIG. 3B, FIG. 3C, FIG. 3D and FIG. 3E) is an explanatory view for illustrating a brief summary of a test for evaluating an axial directional distribution of echo intensities and an axial directional distribution of reception times of an echoes, the test being conducted for a metal seal part of a box.

FIG. 4A illustrates the axial directional distribution of the echo intensities (upper diagram) and the axial directional distribution of the reception times of the echoes (lower diagram) that are obtained when the metal seal parts 12 and 22 are fastened in an adhering state (corresponding to the state of FIG. 3A). As shown in FIG. 3A, in a case of fastening the metal seal parts 12 and 22 in the adhering state, at the center portion of the seal face (namely, area represented by an arrow of a broken line in FIG. 3A), the lubricant is hardly laid and the box 2 and the pin 1 are almost directly accumulated. Therefore, as a result that the ultrasonic wave having propagated to the metal seal part 22 of the box easily transmits toward the pin 1, as shown in FIG. 4A, the axial directional distribution of the echo intensities is obtained such that the echo intensity from the center portion of the seal face (area represented by an arrow of a broken line in FIG. 4A) is lowered. In addition, the axial directional distribution of the reception times of the echoes is obtained such that the reception time of the echo is linearly changed along the seal faces of the metal seal parts 12 and 22. The axial directional distribution of the reception times of the echoes is obtained because the ultrasonic probe for transmitting and receiving the ultrasonic wave is moved in parallel with the axial direction of the threaded joint 100 while the seal faces of the metal seal parts 12 and 22 are formed in a taper to be linearly inclined in the axial direction of the threaded joint 100.

Figure 3B:
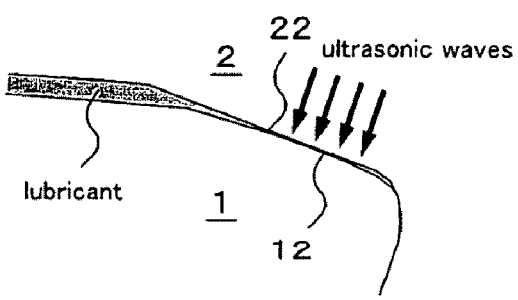

FIG. 4B illustrates the axial directional distribution of the echo intensities (upper diagram) and the axial directional distribution of the reception times of the echoes (lower diagram) that are obtained when the metal seal parts 12 and 22 are fastened in an non-adhering state (corresponding to the state of FIG. 3B). As shown in FIG. 3B, in a case of fastening the metal seal parts 12 and 22 in the non-adhering state, the lubricant is also laid at the center portion of the seal face, and the box 2, the lubricant, and the pin 1 are accumulated into a three-layered structure. Therefore, as a result that the ultrasonic wave having propagated to the metal seal part 22 of the box is mostly reflected from a boundary face between the lubricant and metal seal part 22, as shown in FIG. 4B, the echo intensity from the center portion of the seal face is not lowered, and the axial directional distribution of the echo intensities is obtained such that the echo intensity is higher across the entire area of the metal seal part 22. In addition, the axial directional distribution of the reception times of the echoes is similar to that of a case where the metal seal parts 12 and 22 shown in FIG. 4A are fastened in the adhering state.

Figure 3C:
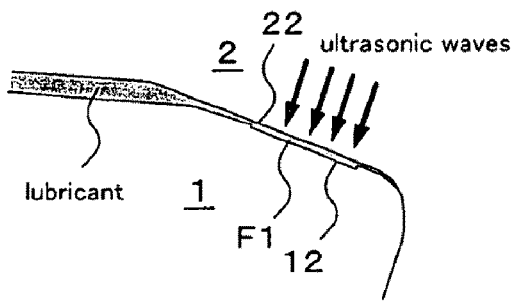

FIG. 4C illustrates the axial directional distribution of the echo intensities (upper diagram) and the axial directional distribution of the reception times of the echoes (lower diagram) that are obtained when the artificial defect F1 is provided on the seal face of the metal seal part 12 (corresponding to the state of FIG. 3C). As shown in FIG. 3C, in a case where the artificial defect F1 is provided on the seal face of the metal seal part 12, the lubricant is filled in the artificial defect F1, and the box 2, the lubricant, and the pin 1 are accumulated into a three-layered structure. Therefore, as shown in FIG. 4C, also when the artificial defect F1 is provided, the axial directional distribution of the echo intensities is similar to that shown in FIG. 4B. In addition, the axial directional distribution of the reception times of the echoes similar to that shown in FIG. 4B is obtained since the ultrasonic wave is reflected from the boundary face between the lubricant and the metal seal part 22 where the artificial defect F1 is not provided.

Figure 3D:
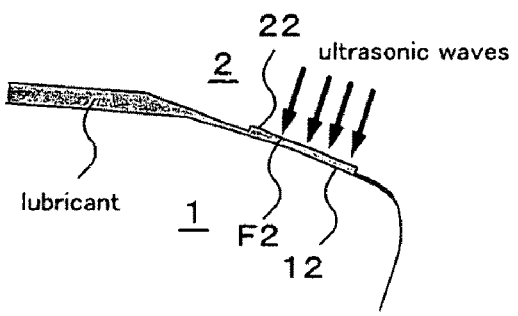

FIG. 4D illustrates the axial directional distribution of the echo intensities (upper diagram) and the axial directional distribution of the reception times of the echoes (lower diagram) that are obtained when the artificial defect F2 is provided on the seal face of the metal seal part 22 (corresponding to the state of FIG. 3D). As shown in FIG. 3D, in a case where the artificial defect F2 is provided on the seal face of the metal seal part 22, the lubricant is filled in the artificial defect F2, and the box 2, the lubricant, and the pin 1 are accumulated into a three-layered structure. Therefore, as shown in FIG. 4D, also when the artificial defect F2 is provided, the axial directional distribution of the echo intensities is similar to that shown in FIG. 4B and FIG. 4C. On the other hand, the reception time of the echo is shortened in accordance with the depth of the artificial defect F2 since the ultrasonic wave is reflected from the boundary face between the lubricant and a bottom portion of the artificial defect F2. In other words, the axial directional distribution of the reception times of the echoes is formed to be shorter (deviated from a straight line) in the area where the artificial defect F2 is provided (namely, area represented by an arrow of a broken line in FIG. 4D).

Figure 3E:
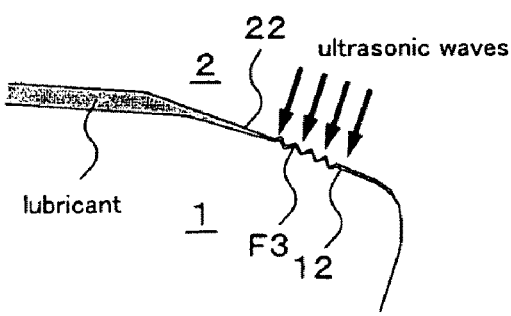

FIG. 4E illustrates the axial directional distribution of the echo intensities (upper diagram) and the axial directional distribution of the reception times of the echoes (lower diagram) that are obtained when the seized portion F3 is generated between the metal seal parts 12 and 22 (corresponding to the state of FIG. 4E). As shown in FIG. 3E, when the seized portion F3 is generated between the metal seal parts 12 and 22, surface natures of the seal faces of the metal seal parts 12, 22 are deteriorated (for example, a surface roughness becomes large), so that it is difficult for the ultrasonic wave to transmit through the seal faces regardless of whether the lubricant is filled between the seal faces or not. Therefore, as shown in FIG. 4E, the axial directional distribution of the echo intensities is made in such a manner that the echo intensity from the center portion of the seal face is not lowered too much (slightly lowered since because of scattering on the seal face), and the echo intensity is relatively large across the entire area of the metal seal part 22. In addition, the axial directional distribution of the reception times of the echoes is made to be shorter (deviated from the straight line) in the area where the seized portion F3 is generated (namely, area represented by an arrow of a broken line in FIG. 4E).

As described above, the inventors of the present invention have found that the lubricant lying at the contact region between the metal seal part 12 of the pin 1 and the metal seal part 22 of the box 2 is not laid locally in a state where the metal seal parts 12 and 22 adhere tightly with each other, unlike the non-adhering state (refer to FIG. 3A and FIG. 3B). Further, the inventors have found that, as a result that the echo intensity of the ultrasonic wave received from the location where the lubricant is not substantially laid is lower than the echo intensity of the ultrasonic wave received from the location where the lubricant is laid, the echo intensity of the ultrasonic wave is lowered locally in a state where the threaded joint is normal and the metal seal parts 12 and 22 adhere tightly with each other, unlike the non-adhering state (refer to the upper diagrams of FIG. 4A and FIG. 4B). In addition, the inventors have found that, in a state where a defect or a seized portion lies in the location where the lubricant would not substantially lie if the threaded joint were normal and the metal seal parts 12 and 22 adhered tightly with each other, the echo intensity of the ultrasonic wave becomes higher as compared to a case where a defect and a seized portion do not lie (refer to the upper diagrams of FIGS. 4C to 4E). Further, the inventors have found that the reception time of the echo from the defect lying in the metal seal part 22 or the echo from the seized portion between the metal seal parts 12 and 22 becomes shorter than the reception time of the echo from the normal threaded joint in the adhering state, the echo from the threaded joint in the non-adhering state, or the echo from the defect lying in the metal seal part 12 (refer to the lower diagrams of FIGS. 4A to 4E).

Further, while the evaluation test conducted with respect to the metal seal part 22 of the box 2 is exemplified in FIG. 3 and FIG. 4, the inventors confirmed that similar results are obtained for the internal thread part 21 and the shoulder part 23.

The present invention has been completed based on the above-described knowledge of the inventors, and the present invention is characterized in that ultrasonic waves are transmitted and received to and from a plurality of locations along the axial direction of the threaded joint 100 in at least one part among the internal thread part 21, the metal seal part 22, and the shoulder part 23 of the box 2 to detect the axial directional distribution of the echo intensities and the axial directional distribution of the reception times of the echoes for the plurality of locations, based on which the abnormal portion (defect, non-adhering portion, and seized portion) lying in the threaded joint 100 is detected.

According to the present invention, by evaluating the axial directional distribution of the echo intensities along the axial direction of the threaded joint 100 with respect to at least one part (part to be evaluated) among the internal thread part 21, the metal seal part 22 and the shoulder part 23, it is possible to detect whether or not there is an area where the echo intensity of the ultrasonic wave is locally lower in the part to be evaluated. Then, when there is the area where the echo intensity of the ultrasonic wave is locally lower in the part to be evaluated, the part to be evaluated of the box and the corresponding part of the pin adhere tightly with each other, so that it is possible to determine that there is no abnormal portion at the contact region. On the other hand, when there is no area where the echo intensity of the ultrasonic wave is locally lower in the part to be evaluated, it is possible to determine that there is an abnormal portion at the contact region between the part to be evaluated of the box and the corresponding part of the pin. Further, by evaluating the axial directional distribution of the reception times of the echoes along the axial direction of the threaded joint 100, it is possible to identify the defect lying in the box and the seized portion between the box and the pin from other abnormal portions.

Hereinafter, specific examples of the ultrasonic testing method according to the present invention (namely, specific examples of the method for detecting an abnormal portion in the part to be evaluated) will be described.

Figure 5A:
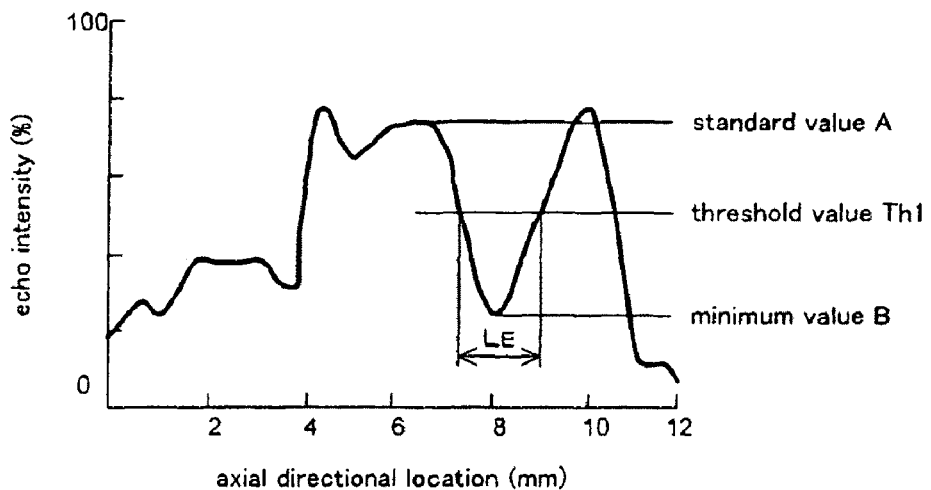
FIG. 5 (FIG. 5A, FIG. 5B and FIG. 5C) is an explanatory view for describing a specific example of a method for detecting an abnormal portion in a case where a part to be evaluated is a metal seal part.
Figure 5B:
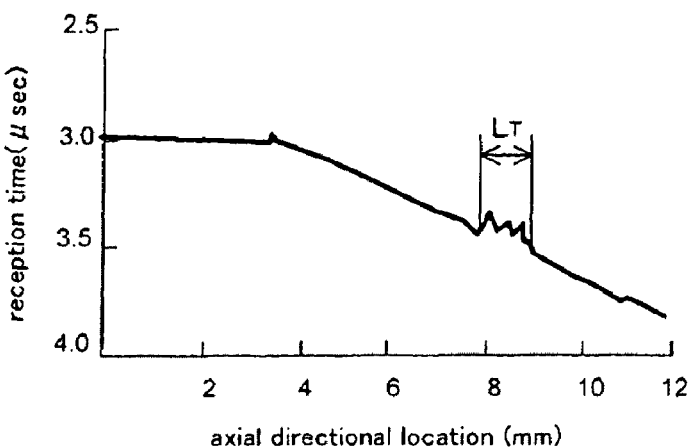
Figure 5C:
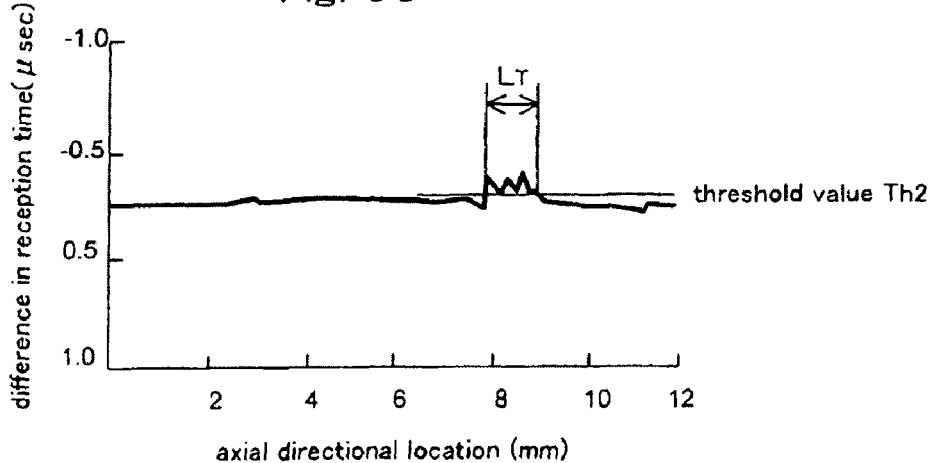

FIG. 5 is an explanatory view for describing a specific example of a method for detecting an abnormal portion when the part to be evaluated is the metal seal part 22. In order to determine whether or not there is an abnormal portion at the contact region of the metal seal parts 12 and 22, as shown in FIG. 5A, with respect to the axial directional distribution of the echo intensities obtained by scanning the ultrasonic wave on the metal seal part 22, a standard value A of the echo intensity that is hardly changed even when the fastening state (adhering state or non-adhering state) is changed and a minimum value B of the echo intensity (minimum value excluding the opposite ends of the axial directional distribution of the echo intensities) are read. Then, when a ratio (B/A) between the minimum value B and the standard value A is larger than a predetermined threshold value that has been decided in advance, it may be determined that there is an abnormal portion. Alternatively, as shown in FIG. 5A, in a case where an axial directional length $L_E$ in an area where the echo intensity is not more than a predetermined threshold value Th1 becomes not more than a predetermined length that has been decided in advance, it is also possible to determine that there is an abnormal portion.

Further, when a frequency of a ultrasonic wave to be transmitted and received (namely, a testing frequency) is made excessively high, it is difficult for the ultrasonic wave to transmit toward the pin 1 irrespective of existence or nonexistence of the abnormal portion lying at the contact region of the metal seal parts 12 and 22. In other words, an excessively high frequency is not preferable since the value B/A and the value of the axial directional length $L_E$ are difficult to be changed irrespective of existence or nonexistence of the abnormal portion. As a result, the frequency of the ultrasonic wave to be transmitted and received is preferably set to be not more than 25 MHz (more preferably, not more than 5 MHz).

In order to identify a kind of the abnormal portion lying at the contact region of the metal seal parts 12 and 22, the axial directional distribution (refer to FIG. 5B) of the reception times of the echoes obtained by scanning the ultrasonic wave on the metal seal part 22 may be used. Specifically, by obtaining a difference between the above obtained axial directional distribution of the reception times of the echoes and the axial directional distribution of the reception times of the echoes that has been obtained in advance (refer to FIG. 5C) for the normal threaded joint in the adhering state, in a case where an axial directional length $L_T$ of the area where the obtained difference exceeds a predetermined threshold value Th2, which has been decided in advance, exceeds a predetermined length, which has been decided in advance, it is possible to determine that there is a defect lying in the box or a seized portion particularly among the abnormal portions. Alternatively, after applying a high-pass filtering processing to the obtained axial directional distribution of the reception times of the echoes (refer to FIG. 5B) to remove a linearly changing component, it may be determined that there is a defect lying in the box or a seized portion particularly among the abnormal portions in a case where the axial directional length of the area exceeding a predetermined threshold value, which has been decided in advance, exceeds a predetermined length, which has been decided in advance.

Hereinafter, description is given to a specific example of an ultrasonic testing apparatus for carrying out an ultrasonic testing method according to the present invention.

Figure 6:
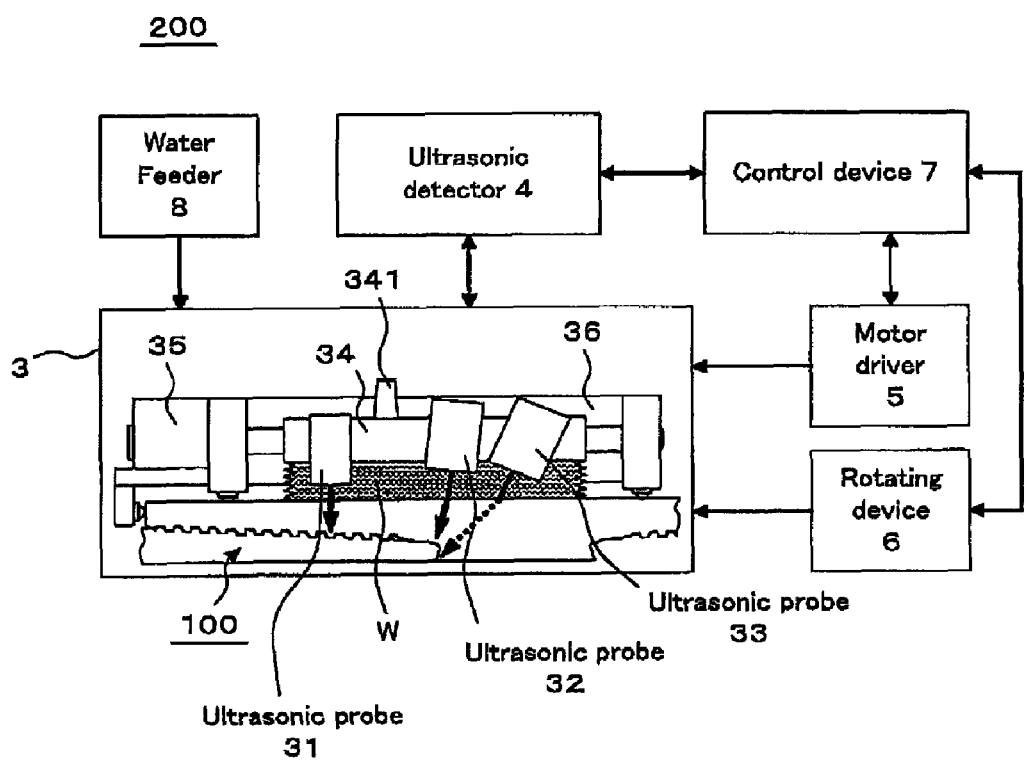
FIG. 6 is a block diagram schematically showing an entire constitution of an ultrasonic testing apparatus for carrying out an ultrasonic testing method according to the present invention.
Figure 7:
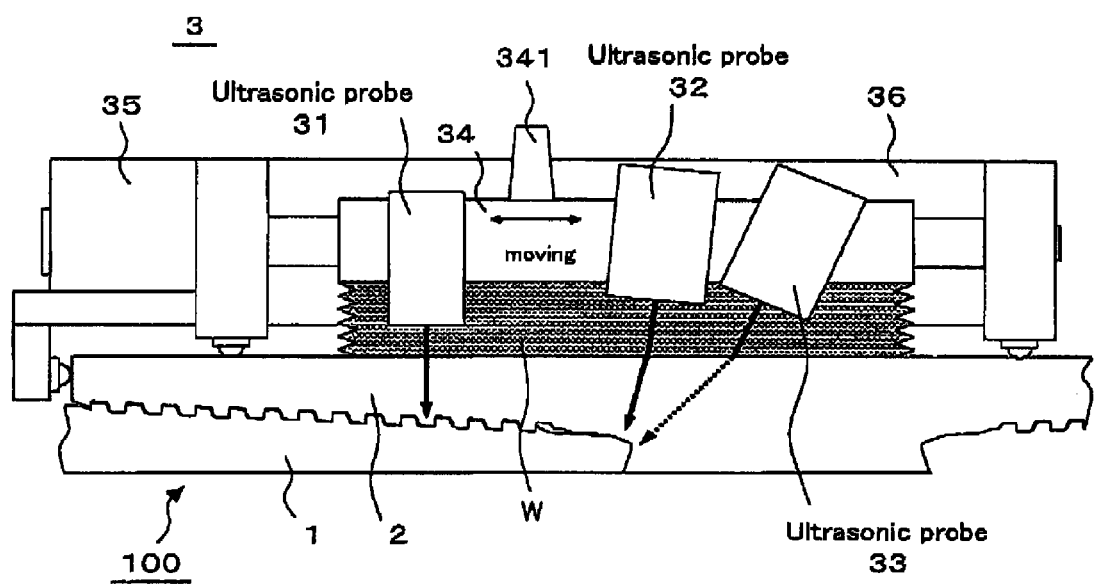
FIG. 7 is a schematic block diagram of an ultrasonic wave scanner forming the ultrasonic testing apparatus.

FIG. 6 is a block diagram schematically showing an entire constitution of an ultrasonic testing apparatus. FIG. 7 is a schematic block diagram of an ultrasonic wave scanner forming the ultrasonic testing apparatus.

As shown in FIG. 6 and FIG. 7, an ultrasonic testing apparatus 200 according to the present specific example comprises an ultrasonic wave scanner 3 for scanning an ultrasonic wave along the axial direction of the threaded joint 100, an ultrasonic detector 4 for controlling transmission and reception of the ultrasonic wave from ultrasonic probes 31, 32, and 33 provided in the ultrasonic wave scanner 3, a motor driver 5 for driving a motor 35 provided in the ultrasonic wave scanner 3, a rotating device 6 for scanning the ultrasonic wave scanner 3 along a circumferential direction of the threaded joint 100 or rotating the threaded joint 100 in a circumferential direction, a control device 7 for controlling the ultrasonic detector 4, the motor driver 5 and the rotating device 6, and a water feeder 8 for feeding water as a contact medium of the ultrasonic wave.

The ultrasonic wave scanner 3 comprises the ultrasonic probe 31 for carrying out ultrasonic testing of the thread parts 11 and 21, the ultrasonic probe 32 for carrying out ultrasonic testing of the metal seal parts 12 and 22, and the ultrasonic probe 33 for carrying out ultrasonic testing of the shoulder parts 13 and 23. As the ultrasonic probe 31, for example, the constitution of vertically transmitting and receiving the ultrasonic wave so as to be focused on an apex of a screw root of the internal thread part 21 can be employed by using an immersion probe (frequency: 3.5 MHz, transducer diameter: about 13 mm, focal distance: about 38 mm, point focus probe). As the ultrasonic probe 32, it possible to use the ultrasonic probe similar to that used for the evaluation test obtaining the result shown in FIG. 4. Further, as the ultrasonic probe 32, it is possible to employ the constitution of transmitting and receiving an ultrasonic wave so as to be focused on a corner part 231 (refer to FIG. 1) of the shoulder part 23, by using an immersion probe (frequency: 5 MHz, transducer diameter: about 19 mm, focal distance: about 64 mm, point focus probe). Then, the angle of the ultrasonic probe 33 may be adjusted so that the ultrasonic shear wave having an angle of refraction in the range of about 35° to 45° is propagated into the box 2. Further, it is preferable that the diameter of the focused ultrasonic wave beam (ultrasonic wave beam diameter on a focal point) is as small as possible. For example, in a case of the ultrasonic probe 32, it is preferable that the ultrasonic wave beam diameter on the focal point is about not more than 1 mm because the axial directional length of highly adhering portion (portion where there is substantially no lubricant) of the metal seal parts 12 and 22 is about 1 mm.

The ultrasonic wave scanner 3 comprises a probe holder 34, a motor 35, and a table 36 on which the probe holder 34 and the motor 35 are attached, in addition to the ultrasonic probes 31 to 33.

The ultrasonic probes 31, 32, and 33 are mounted to the probe holder 34. The probe holder 34 also has a function of filling water W as a contact medium that is fed from the water feeder 8 and flows from a water feeding port 341 into a gap between the ultrasonic probes 31 to 33 and the outer surface of the box 2 of the threaded joint 100. Rotational motive energy of the motor 35 is transmitted to the probe holder 34 via an appropriate mechanical element for converting this rotational motive energy into a linear motion, and the probe holder 34 can thereby move along the axial direction of the threaded joint 100. Due to movement of the probe holder 34, also the ultrasonic probes 31, 32, and 33 mounted to the probe holder 34 move along the axial direction of the threaded joint 100, and the transmission and reception positions of the ultrasonic wave is thereby scanned along the axial direction of the threaded joint 100. In this state, since the table 36 holds a state of contacting the threaded joint 100 (box 2), a distance between the probe holder 34 mounted to the table 36 and the outer surface of the box 2, and further, distances between the ultrasonic probes 31, 32, and 33 and the outer surface of the box 2 can be kept constantly. Then, since the table 36 or the threaded joint 100 are rotated in the circumferential direction by the rotating device 6, it is possible to transmit and receive the ultrasonic wave to and from a plurality of locations in the circumferential direction of the threaded joint 100.

FIG. 8 illustrates an example of a result of carrying out the ultrasonic testing of the metal seal part 22 in an adhering state by using the ultrasonic testing apparatus 200 having the above-described constitution. On each of the seal faces of the metal seal parts 12 and 22 of the box (outer diameter: about 150 mm, inner diameter: about 125 mm), an artificial defect (slit) is provided, which has an axial directional length of 2 mm, a circumferential length of 3 mm, and a depth of 0.5 mm. According to the example shown in FIG. 8, the echo intensity distribution of the entire circumference is measured with a pitch of 12 mm in the axial direction of the threaded joint 100 and a pitch of 1° in the circumferential direction. FIG. 8A illustrates a C scope that is represented by dark and light depending on the volume of the echo intensity on each measuring point with a lateral axis in the axial direction and a longitudinal axis in the circumferential direction, and FIG. 8B illustrates the axial directional distribution of the echo intensities and the axial directional distribution of the reception times of the echoes from a normal portion, in the vicinity of the defect provided on the pin side (provided on the side of the metal seal part 12), and in the vicinity of the defect provided on the box side (provided on the side of the metal seal part 22).

As shown in FIG. 8A, in the area other than the area where a defect upon fastening lies (namely, a defect to be generated on the outer surface of the box 2 by holding the box 2 with a tool upon fastening) and the area where the artificial defect is provided, the echo intensity is obtained mostly evenly in a circumferential direction. On the other hand, as shown in FIG. 8B, it is found that the axial directional distribution of the echo intensities in the normal portion is obtained in such a manner that the echo intensity is lower on the almost center portion of the metal seal part. To the contrary, the axial directional distribution of the echo intensities in the vicinity of the defect on the pin side (near the circumferential directional position of 180°) and in the vicinity of the defect on the box side (near the circumferential directional position of 90°) has no area where the echo intensity is locally lower unlike the normal portion, so that it is found that the defect can be detected in accordance with this difference in distribution. In addition, the reception time of the echo is shorted in the area where there is a defect in the vicinity of the defect on the box side, while the axial directional distribution is linearly changed in the vicinity of the defect on the pin side. Therefore, due to this difference in distribution, it is found to be capable of identifying whether the pin or the box has the defect. Further, in a case where there is a non-adhering portion between the pin 1 and the box 2, the axial directional distribution of the echo intensities and the axial directional distribution of the reception times of the echoes at this non-adhering portion indicate tendency similar to that of the vicinity of the defect on the pin side. However, the non-adhering portion often lies continuously in the circumferential direction of the threaded joint 100 unlike the defect, so that, by evaluating the both of the axial directional distribution of the echo intensities and the circumferential directional distribution of the echo intensities, it is considered that the defect on the pin side can be identified from the non-adhering portion.

Figure 9:
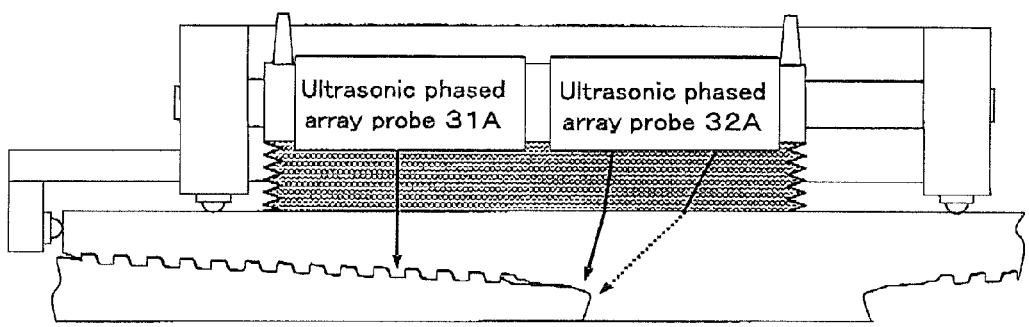
FIG. 9 is a schematic block diagram of an ultrasonic wave scanner according to another example.

The ultrasonic wave scanner is not limited to the constitution shown in FIG. 7, and for example, the constitution including an ultrasonic phased array probe as shown in FIG. 9 (according to the example shown in FIG. 9, an ultrasonic phased array probe 31A for carrying out ultrasonic testing of the thread parts 11 and 21, and an ultrasonic phased array probe 32A for carrying out ultrasonic testing of the metal seal parts 12 and 22 and the shoulder parts 13 and 23) can be also employed. Then, by electrically controlling transmission and reception of the ultrasonic wave by the respective transducers of the ultrasonic phased array probes 31A and 32A in a conventional manner, the ultrasonic wave to be transmitted and received may be scanned in the axial direction of the threaded joint 100.

The invention claimed is:

1. An ultrasonic testing method of a threaded joint of pipes or tubes including a pin having an external thread part, a metal seal part, and a shoulder part on an outer peripheral surface, and a box having an internal thread part, a metal seal part, and a shoulder part corresponding to each part of the pin on an inner peripheral surface and being fastened with the pin by way of a lubricant, the method comprising the steps of:

transmitting and receiving ultrasonic waves to and from a plurality of locations along a longitudinal axial direction of the threaded joint in at least one of the internal thread part, the metal seal part, and the shoulder part of the box;

detecting echo intensities and reception times of echoes for the plurality of locations; and detecting an abnormal portion in the threaded joint based on longitudinal axial directional distribution of the echo intensities and longitudinal axial directional distribution of reception times of the echoes.

2. The ultrasonic testing method of the threaded joint of pipes or tubes according to claim 1, wherein the ultrasonic waves are transmitted and received to and from the plurality of locations along the longitudinal axial direction of the threaded joint in at least one part of the box by relatively moving an ultrasonic probe in the longitudinal axial direction of the threaded joint.

3. The ultrasonic testing method of the threaded joint of pipes or tubes according to claim 1, wherein the ultrasonic waves are transmitted and received to and from the plurality of locations along the longitudinal axial direction of the threaded joint in at least one part of the box by electrically controlling the transmission and reception of the ultrasonic wave by each transducer of an ultrasonic phased array probe in which a plurality of transducers are arrayed.

* * * * *